(12) United States Patent
Lomas

(10) Patent No.: US 7,575,719 B2
(45) Date of Patent: Aug. 18, 2009

(54) CENTRIFUGATION DEVICE

(75) Inventor: Peter Lomas, Bebington (GB)

(73) Assignee: Thermo Shandon Limited, Cheshire (GB)

( * ) Notice: Subject to any disclaimer, the term of this patent is extended or adjusted under 35 U.S.C. 154(b) by 447 days.

(21) Appl. No.: 10/569,705

(22) PCT Filed: May 5, 2004

(86) PCT No.: PCT/GB2004/001904

§ 371 (c)(1),
(2), (4) Date: Mar. 27, 2006

(87) PCT Pub. No.: WO2005/019806

PCT Pub. Date: Mar. 3, 2005

(65) Prior Publication Data

US 2007/0003439 A1 Jan. 4, 2007

(30) Foreign Application Priority Data

Aug. 21, 2003 (GB) ................................ 0319709.2

(51) Int. Cl.
*G01N 9/30* (2006.01)
(52) U.S. Cl. ................. 422/72; 422/99; 422/100; 422/101; 422/102; 436/177; 436/178; 436/180
(58) Field of Classification Search ............ 422/72, 422/99–102; 436/177–178, 180
See application file for complete search history.

(56) References Cited

U.S. PATENT DOCUMENTS 4,853,188 A * 8/1989 Toya ..................... 427/2.11
5,470,758 A * 11/1995 Hayes ..................... 436/177
5,952,239 A * 9/1999 Hayes et al. ............. 436/177

* cited by examiner

*Primary Examiner*—Jill Warden
*Assistant Examiner*—Jyoti Nagpaul
(74) *Attorney, Agent, or Firm*—Thomas A. Runk; Fulwider Patton LLP

(57) ABSTRACT

A centrifugation device comprising a combined sample chamber and slide holder adapted to be mounted, with a microscope slide, in a centrifuge in a predetermined position, after placing, in the sample chamber, a fluid biological sample containing cells, the centrifugation device comprising a body (10) affording a base (14) adapted for engagement with a microscope slide, structure on one side of the base defining a chamber for a fluid sample, with an opening (15) for the introduction of fluid to said chamber, the base (14) including an aperture (18) and carrying a means for sealing the edges of such aperture with respect to the surface of a microscope slide placed across the base (14), or for allowing the passage of liquid but obstructing the passage of cells, the centrifugation device further including a back plate (12) arranged, when the back plate (12) is closed against the rear of a microscope slide engaged with the base (14), to locate the slide between the base and the cover plate and to hold the cover plate in this closed position, wherein said base (14) comprises a supporting frame (17) and, within said support frame, a pressure plate (19) provided with said aperture (18), and wherein the pressure plate is supported from said frame by flexible resilient means (40, 42) such as to allow the pressure plate to "float" and to align itself with a microscope slide located between the pressure plate and the back plate as the back plate is closed.

4 Claims, 6 Drawing Sheets

CENTRIFUGATION DEVICE

RELATED APPLICATIONS

Figure 1:
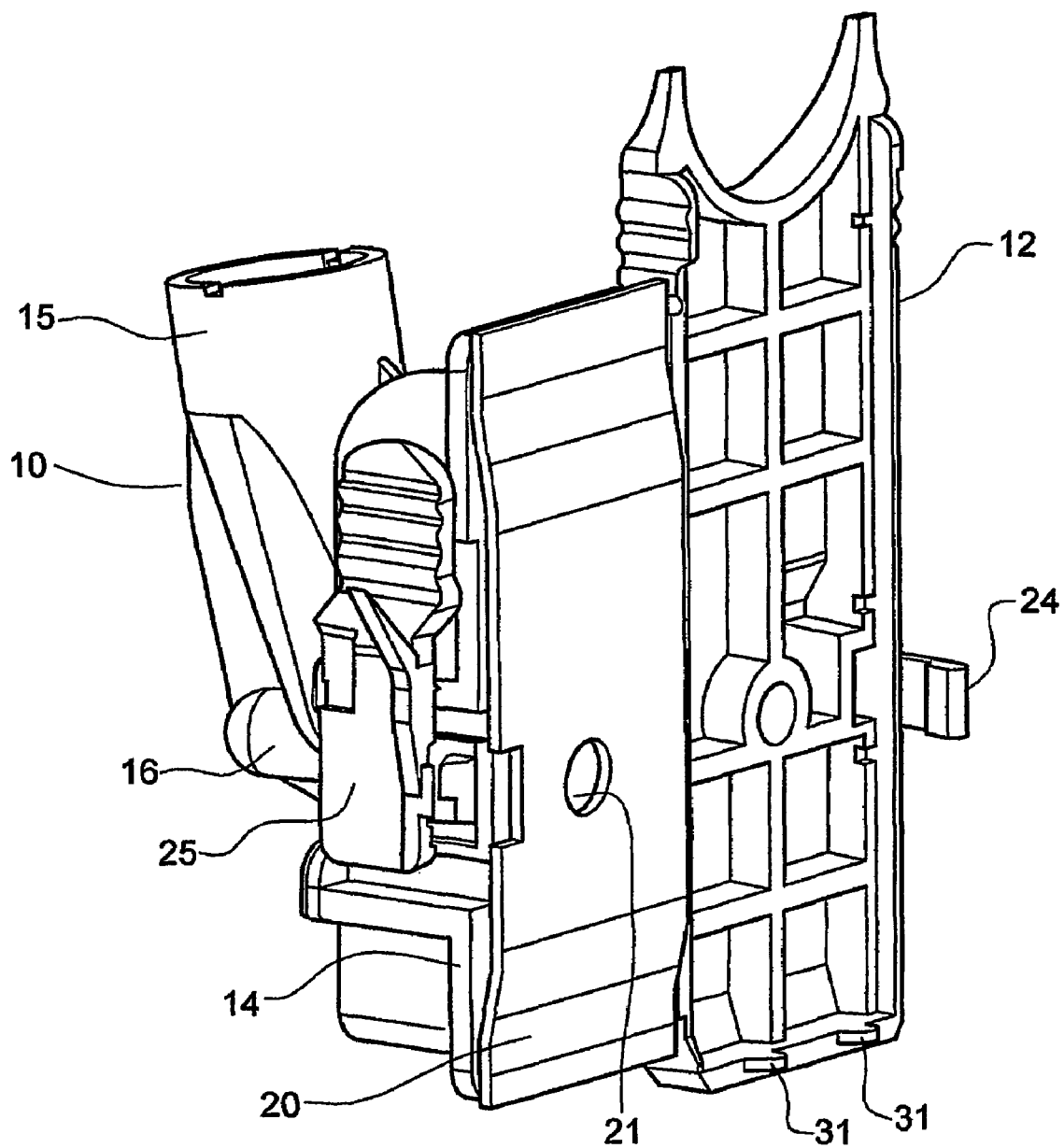

This is a U.S. national phase of PCT/GB2004/001904 filed 5 May 2004, claiming priority from GB 0319709.2 filed 21 Aug. 2003.

THIS INVENTION relates to a centrifugation device comprising a combined sample chamber and slide holder adapted to be mounted, with a microscope slide, in a centrifuge in a predetermined position, after placing, in the sample chamber, a fluid biological sample containing cells, the device being so-arranged that when the centrifuge is operated, a thin layer—ideally a monolayer—of cells is deposited from the fluid-onto a predetermined deposition area on the glass microscope slide; Such a centrifugation device is herein referred to as being "of the kind specified".

Various forms of centrifugation device of the kind specified have been known in the past. Examples of such devices are disclosed, for example, in U.S. Pat. Nos. 4,391,710; 4,696,743; 4,853,188 and 4,874,582 and European Patents Nos. 0184374 and 0047840. Some examples have been reusable, that is to say it was possible and intended that after the device had been used to deposit cells from a fluid sample onto a first microscope slide, and the slide removed, the device could be cleaned, a fresh slide fitted, a fresh fluid sample placed in the sample chamber and the device again placed into the centrifuge and so on indefinitely. In these arrangements the slide is, of course retained by a releasable and re-attachable clip of some description. Some later centrifugation devices of the kind specified were of the single-use type, that is to say they were designed in such a way that they could not, or could not conveniently, be used more than once, thereby avoiding contamination problems resulting from improper cleaning procedures between uses. In view of their inevitably disposable nature, devices of the latter character have generally been largely of plastics in order to minimise production costs.

A centrifugation device of the kind specified generally comprises a combined sample chamber and slide holder adapted to be mounted, with a microscope slide, in a predetermined position in a centrifuge after placing, in the sample chamber, a fluid biological sample containing cells, the centrifugation device comprising a body affording a base adapted for engagement with such microscope slide, structure on one side of the base defining the sample chamber with an opening for the introduction of fluid to the sample chamber, the base including an aperture for communicating with the sample chamber and the base carrying means for sealing the edges of such aperture with respect to the surface of the microscope slide placed across the base, or for allowing the passage of liquid but obstructing the passage of cells. Such a centrifugation device further typically includes, a back plate hingedly connected with the base, or otherwise securable to the base.

A problem which arises, particularly in relation to single use, moulded plastics centrifugation devices of the kind specified, is that of ensuring effective sealing or quasi-sealing of the edge of said aperture communicating with the sample chamber with respect to the slide. The Applicants have proposed, in co-pending UK Patent Application No. 0301047.7 to use an elastomeric gasket around said aperture to effect a seal with respect to the slide. However, in the past, it has been common to interpose between the slide and the base of the device in which the said aperture is provided, a sheet of liquid-absorbent paper or card, with a hole therein which is aligned with the aperture in said base of the centrifugation device and which serves to absorb liquid from the sample whilst blocking passage of cells, etc. which are to be deposited on the slide. Such a filter card arrangement is still preferred for small capacity centrifugation devices of the kind specified. However, because of limited compressibility of the filter card paper used, correct alignment of the surface of the said base which in the closed position provides engages the and provides support for the filter card held against the slide surface, good alignment of that surface with the opposing slide surface is necessary if leakage of fluid, (and/or cell material) past the filter card is to be avoided.

It is an object of the present invention to provide an improved centrifugation device.

According to one aspect of the invention there is provided a centrifugation device comprising a combined sample chamber and slide holder adapted to be mounted, with a microscope slide, in a centrifuge in a predetermined position, after placing, in the sample chamber, a fluid biological sample containing cells, the centrifugation device comprising a body affording a base adapted for engagement with a microscope slide, structure on one side of the base defining a chamber for a fluid sample, with an opening for the introduction of fluid to said chamber, the base including an aperture and carrying a means for sealing the edges of such aperture with respect to the surface of a microscope slide placed across the base, or for allowing the passage of liquid but obstructing the passage of cells, the centrifugation device further including a back plate arranged, when the back plate is closed against the rear of a microscope slide engaged with the base, to locate the slide between the base and the cover plate and to hold the cover plate in this closed position, wherein said base comprises a supporting frame and, within said supporting frame, a pressure plate provided with said aperture, and wherein the pressure plate is supported from said frame by flexible resilient means such as to allow the pressure plate to "float" and to align itself with a microscope slide located between the pressure plate and the back plate as the back plate is closed.

An embodiment of the invention is described below by way of example with reference to the accompanying drawings in which:—

FIG. 1 is a perspective view from the rear, of a centrifugation device in accordance with the invention in a condition in which a back plate is open relative to a body part, the body part being fitted with a filter card.

Figure 2:
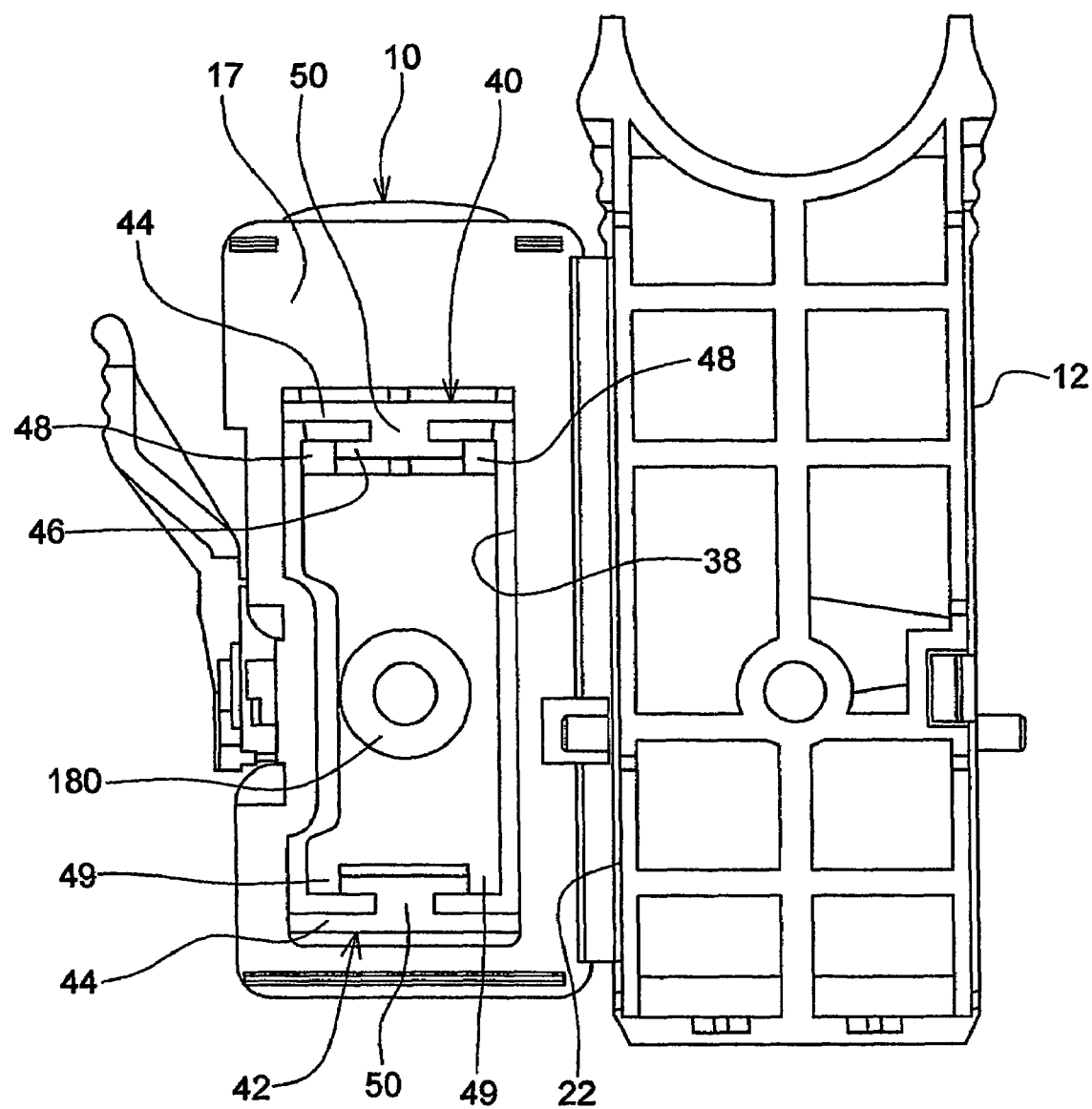
Figure 3:
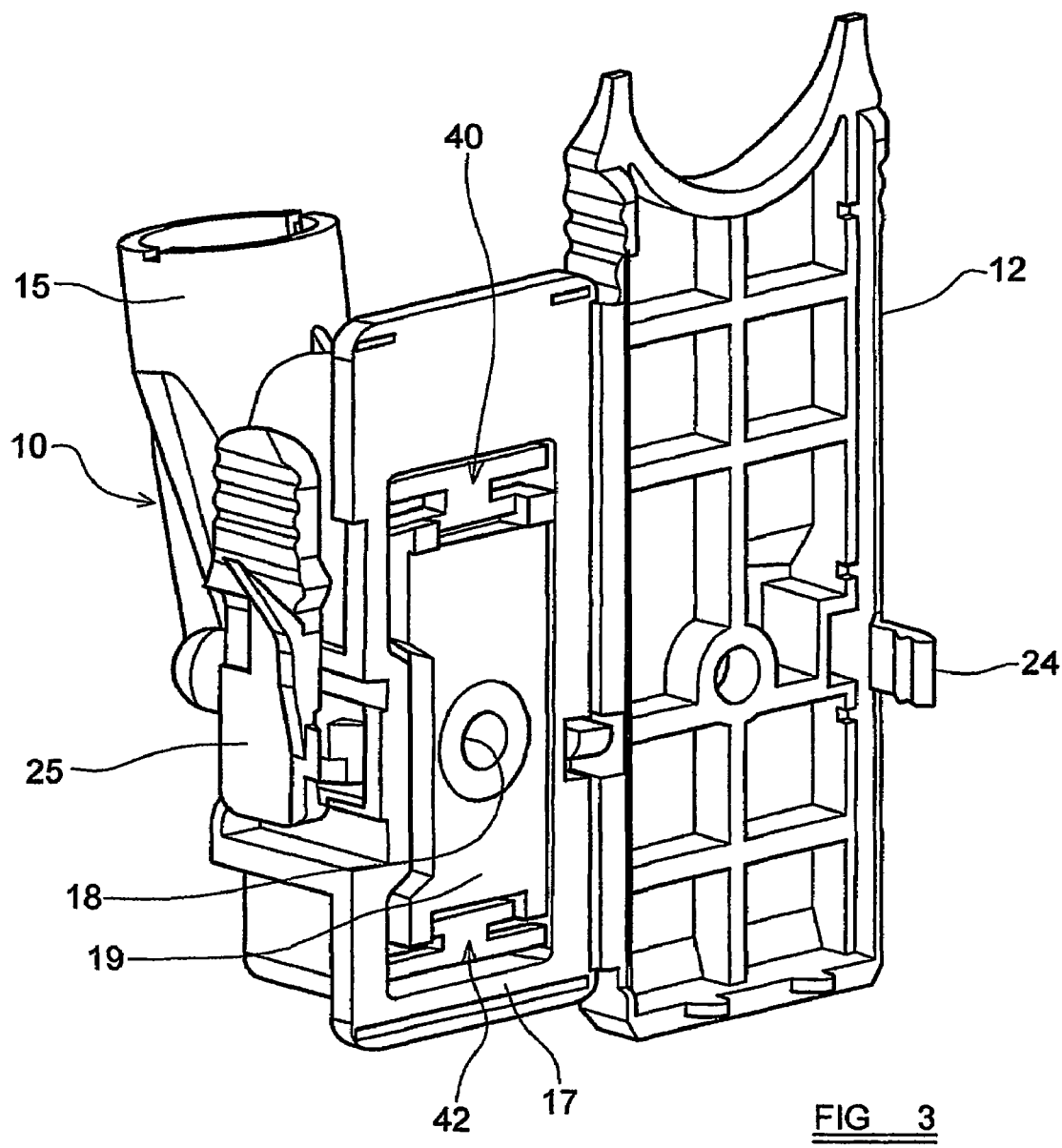
Figure 4:
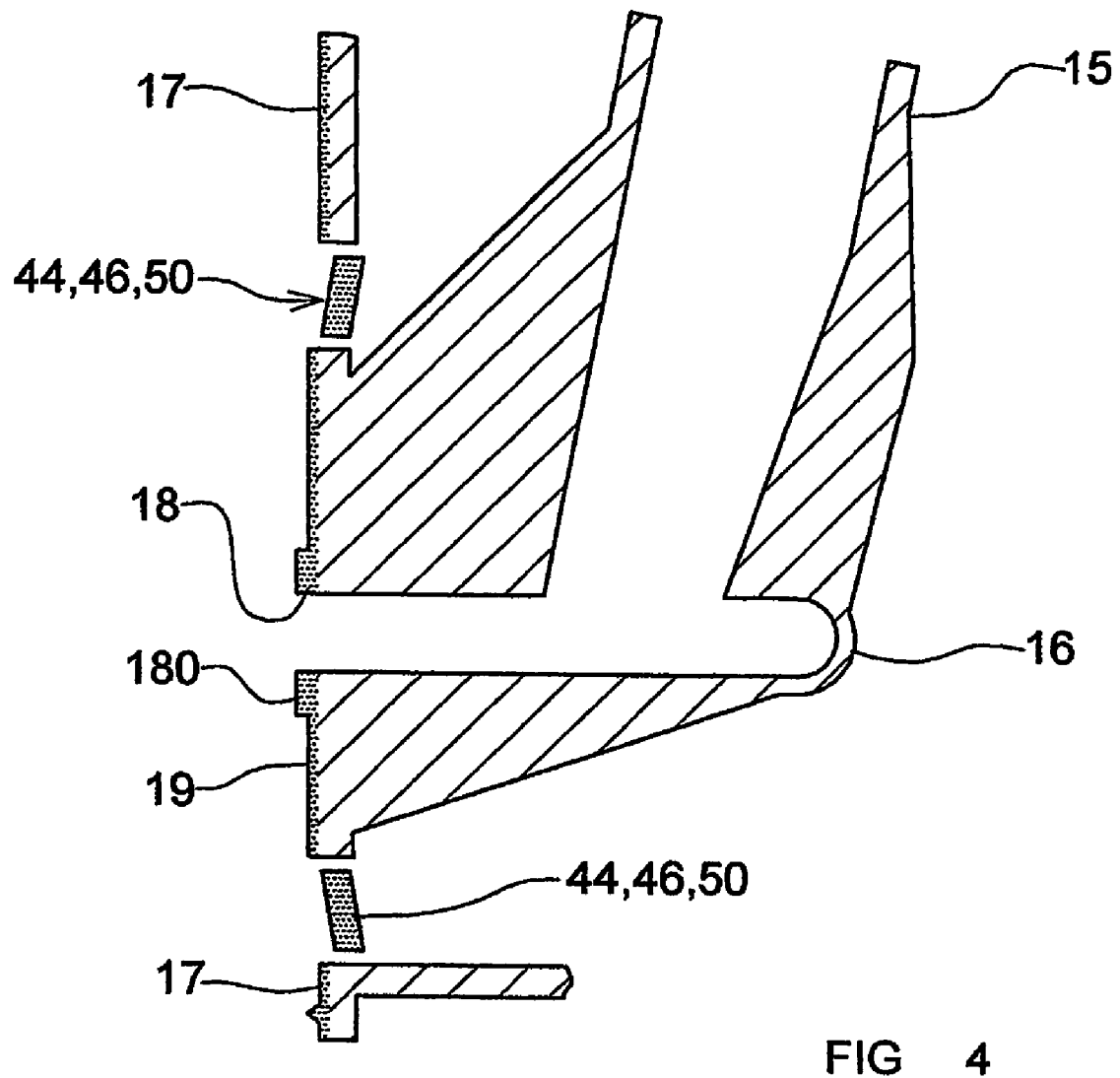
Figure 5:
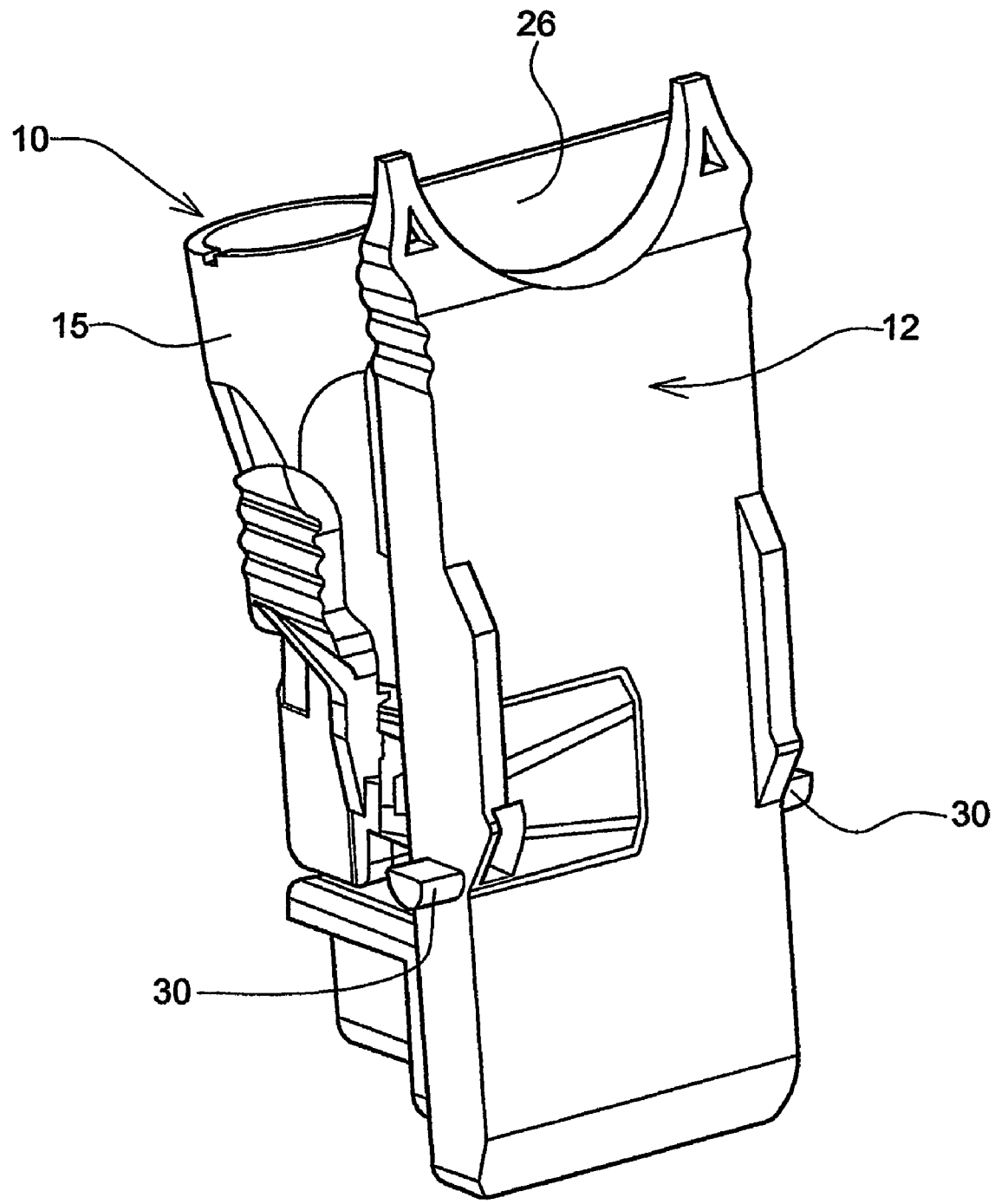

FIG. 2 is a rear elevation view to a larger scale of the centrifugation device of FIG. 1, also in the open condition, with the filter card omitted, FIG. 3 is a perspective view corresponding to FIG. 1 but with the filter card omitted, FIG. 4 is a partial view in vertical section of the body part of the device of FIGS. 1 to 3, and FIG. 5 is a partial perspective view, from the rear and above, of the centrifugation device of FIGS. 1 to 4 in the condition in which the back plate is closed against the body part, with a microscope slide located therebetween.

Figure 6:
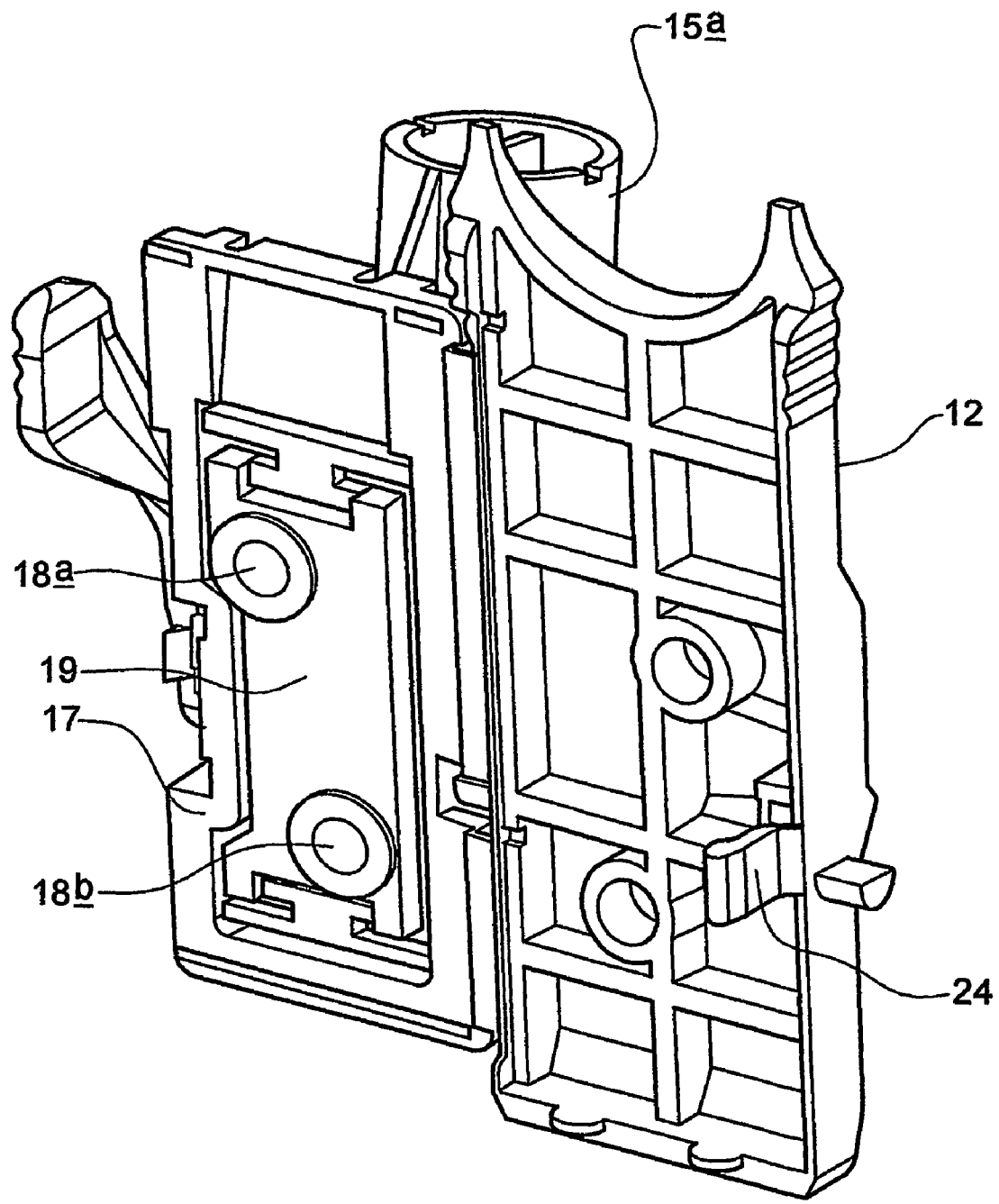

FIG. 6 is a perspective view, with a back plate in an open position, of a variant of the centrifugation device of FIGS. 1 to 4.

Referring to FIGS. 1 to 5, a centrifugation device in accordance with the present invention comprises a body part 10 and a back plate 12 formed integrally with one another by moulding in a suitable plastics material such as polypropylene, the back plate 12 being connected with the body part 10 by way of an integral "living hinge" 22. As shown in FIGS. 1 to 5, the body part 10 comprises a base 14 which, as described below, comprises a frame 17 bounding a plate 19 which carries on its front side integral structure providing a sample chamber 16 which is closed at its end remote from the base 14 and which terminates, in the plane of the plate 19, in an aperture or port 18. A funnel 15 extends upwardly from an entrance opening in the sample chamber, whereby a fluid sample can be introduced into the sample chamber 16.

The base 14 is generally rectangular, as is the back plate 12, and the living hinge 22 extends along one vertical edge of the base 14, more particularly along one vertical edge of the frame 17, and the adjacent vertical edge of the back plate 12. The vertical edge of the back plate 12 remote from the living hinge 22 carries a detent 24 for co-operating with elements 25 carried by the body 10 adjacent the edge of the base 14 remote from the living hinge 22 and which elements, together with detent 24, form a catch arrangement whereby the back plate may be secured in a closed position on the base 14 with a microscope slide, indicated at 26 in FIG. 5, held between the base 14 and the back plate 12. As illustrated, the upper edge of the back plate 12 may be scalloped or recessed, as indicated, to allow ready grasping of the upper edge of the microscope slide 26 between finger and thumb during removal of the slide from the device after centrifugation, as described below. A filter card 20 is fixed to the rear surface of frame 17 and extends over the plate 19. The filter card 20 comprises a sheet of liquid-absorbent card or paper, which is secured, for example, by ultrasonic welding, at its upper and lower ends, (as viewed in FIG. 1) to the frame 17 and extends over the counter plate 19. The filter card 20 has an aperture 21 therein which corresponds in size, shape and position to the port 18 and is aligned therewith.

In use of the device, a microscope slide 26 is located between the back plate 12 and the filter card on the base 14. (FIGS. 1 to 3 show integral lugs 31 to support the lower end of a microscope slide 26 fitted against the front surface of the back plate 12 until the back plate 12, with the slide, is closed against the base 14).

The device is then mounted in a centrifuge (not shown) in such a manner that bosses 30 projecting from the sides of the back plate act as journals received in bearings provided by complementary slots in mounting structure within the centrifuge. When the centrifuge is at rest, the device rests in the centrifuge in a position in which the slide 26 is at an angle. When the centrifuge is spun up, the device pivots about the axis of bosses 30, into a position in which the slide is vertical. When the centrifuge is spun, the centrifugal force generated produces a rapid settling of the cells within the biological sample against the surface of the glass slide 26, within an area bounded by the edges of port 18 and the aperture 21 in the card 20 and these cells remain in a thin layer on the slide after the centrifuge is stopped. After the centrifuge is stopped, the centrifugation device is removed from the centrifuge, and the slide carefully removed after opening of the back plate. The catch arrangement 24,25 is preferably so devised, for example as described in our co-pending UK Patent Application GB0301047.7, that the process of opening the back plate fractures part of the catch arrangement and ensures that the centrifugation device cannot be re-used.

As noted above, the base 14 comprises a peripheral frame 17 and a central panel or counter plate 19 which is mounted with respect to the frame 17 in such a manner as to allow movement of the counter plate 19 with respect to the frame 17. Both the frame 17 and the counter plate 19 have substantially planar rearwardly facing surfaces, i.e. surfaces which face away from the sample chamber 16, and in the unstressed condition of the counter plate 19 and the mounting means therefor, the rear surface of the counter plate is generally parallel with but spaced slightly rearwardly of the plane of the rear surface of the frame 17, as shown in FIG. 4. The sample chamber 16 and funnel 15 are preferably substantially rigid with counter plate 19 and can move slightly, with the counter plate 19, relative to the peripheral frame 17.

Ideally, in the closed condition of the device, in order to ensure that there is no gap between the filter card and the edge of the port 18 or between the filter card in the region around the aperture 21 and the slide 26, through which the cell component of the sample as well as the liquid component might leak, the slide should bear evenly on the filter paper all around the periphery of the aperture 21 and the part of the counter plate around the aperture 18 should likewise bear evenly against the filter paper. Thus, ideally, the relevant parts of the counter plate and the slide, and the portions of the back plate bearing against the slide, should be substantially parallel with one another to achieve this condition. Furthermore, in the regions, of the apertures 18 and 21, there should be controlled force pressing the slide against the filter card and hence against the counter plate. In order to achieve these conditions despite inevitable manufacturing tolerances, the counter plate 19, as mentioned above, is mounted within the frame 17 in such a way as to allow the counter plate to "float" i.e. to adjust its position slightly in relation to the frame 17. As best shown in FIG. 2, this is achieved as follows.

The frame 17 takes the form of a generally rectangular plate which preferably has stiffening structures (not shown in detail), extending from and integral with the front of that plate, i.e. extending generally in the direction in which the sample chamber extends from the counter plate. The counter plate 19 and the support or suspension means therefor are mounted in a generally rectangular aperture 38 in the frame 17 by a respective torsion bar arrangement 40, 42 respectively at the upper or lower end of aperture 38, (as viewed in FIG. 2), the counter plate 19 having a profile complementary with that of the aperture 38 and being mounted with a generally uniform gap between the side edges of the counter plate 19 and the adjacent edges of aperture 38 and with a larger gap, accommodating the respective torsion bar arrangement, between the upper edge of the plate 19 and the upper edge of the aperture 38 and between the lower edge of plate 19 and the lower edge of the aperture 38. In the arrangement illustrated, each torsion bar arrangement comprises a first bar 44, adjacent the respective upper or lower edge of the aperture 38 and spanning the aperture 38 from one side edge of that aperture to the other, a second, parallel bar 46, spanning the space between two lugs 48 at the upper corners or two lugs 49 at the lower corners respectively of the counter plate 19, and an intermediate web 50, much narrower than the counter plate 19 and thus extending along only over a limited middle portion of the first and second bars 44, 46.

As illustrated in FIG. 4, in the unstressed position of the parts of the device, with the back plate 12 in the open position, the rear surface of the counter plate 19 is, as previously noted, set rearwardly somewhat relatively to the rear surface of the frame 17. In this position, however, the rear surface of the counter plate is still generally parallel with the rear surface of the frame 17. When the back plate is moved into the closed position with the slide and the filter card 20 interposed between the back plate and the counter plate and frame, the filter card being interposed between the slide and the counter plate 19 and frame, the counter plate 19 is displaced forwardly relative to the frame 17 by the pressure applied by the back plate via the slide and the filter card, this displacement being permitted by resilient twisting and flexing of the torsion bars, particularly the longer torsion bars 44 and 46. Should it occur that, due, for example, to manufacturing inaccuracies, the position in which the slide is supported by the back plate in the closed position of the back plate is not precisely parallel with the rear face of the frame 17, or that, in the unstressed position, the rear face of the counter plate 19 is not quite parallel with the rear face of the frame 17, differential flexing of the upper and -lower torsion bars 44, 46 and, if necessary, a measure of transverse twisting; (i.e. about a vertical axis as viewed in FIG. 2) of the webs 50 of the torsion bar arrangements, allows the counter plate 19 to align itself into perfect register with the slide/filter card combination. The ease with which the counter plate 19 may be twisted about a vertical axis as viewed in FIG. 2 depends largely upon the transverse extent—i.e. the extent parallel with the longer torsion bars—of the webs 50 connecting the longer and shorter torsion bars 44 and 46 and need generally be somewhat less than the flexibility of each torsion bar arrangement about horizontal axes.

Whilst, in the above, the front face of the rear cover and the rear face of the frame and counter plate have been described as being generally planar, it may be advantageous, in order to secure firm clamping of the slide glass and the filter card between the counter plate and the rear cover, to provide, around the port 18, an annular region 180 standing slightly proud of the remainder of the rear surface of the counter plate and to form the back plate 12, as shown, on its forward side, with a plurality of ribs extending horizontally and vertically, with an annular or cylindrical rib 182 positioned for alignment with the annular region 180 in the closed position of the back plate, with the front surfaces of the horizontal and vertical ribs and the annular region 182 alone lying in a common plane for engagement with the rear surface of the slide 26.

FIG. 6 illustrates a variant of the device of FIGS. 1 to 5 which differs from that of FIGS. 1 to 5 in that there are two sample chambers (not shown) terminating in respective apertures or ports 18*a*, 18*b*, in the counter plate 19 and connected with respective funnels (defined by distinct and mutually isolated parts of a unitary funnel structure 15*a*). The variant of FIG. 6 is intended to be used with a filter card (not shown) having respective apertures aligned with the ports 18*a*, 18*b*.

The frame, counter plate and torsion bar arrangements in the embodiments described are preferably formed in one piece, with the remainder of the centrifugation device, as a unitary injection moulding in a suitable plastics material such as polypropylene.

The invention claimed is:

1. A centrifugation device comprising a combined sample chamber and slide holder adapted to be mounted, with a microscope slide, in a centrifuge in a predetermined position, after placing, in the sample chamber, a fluid biological sample containing cells, the microscope slide having a rear, the centrifugation device comprising a body affording a base adapted for engagement with a microscope slide, structure on one side of the base defining a chamber for a fluid sample, with an opening for the introduction of fluid to said chamber, the base including an aperture and carrying a means for sealing the edges of such aperture with respect to the surface of a microscope slide placed across the base, or for allowing the passage of liquid but obstructing the passage of cells, the centrifugation device further including a back plate arranged, when the back plate is closed against the rear of a microscope slide engaged with the base, to locate the slide between the base and the back plate and to hold the back plate in this closed position, wherein said base comprises a supporting frame and, within said supporting frame, a pressure plate provided with said aperture, and wherein the pressure plate is supported from said frame by flexible resilient means such as to allow the pressure plate to "float" and to align itself with a microscope slide located between the pressure plate and the back plate as the back plate is closed.

2. A centrifugation device according to claim 1 wherein said flexible resilient mounting means is such as to allow the pressure plate to tilt about two mutually perpendicular axes generally parallel with the plane of the frame, with the plane of the major surfaces of such microscope slide in the closed position of the device.

3. A centrifugation device according to claim 2 wherein said resilient flexible suspension means comprises a torsion bar arrangement moulded integrally with the remainder of the device.

4. A centrifugation device according to claim 1 wherein said resilient flexible suspension means comprises a torsion bar arrangement moulded integrally with the remainder of the device.

* * * * *